United States Patent [19]

Sommerdijk et al.

[11] 4,089,799
[45] May 16, 1978

[54] LUMINESCENT FLUORIDE

[75] Inventors: Johannes Leonardus Sommerdijk; Francisca Maria Johanna Henrica Hoex-Strik, both of Eindhoven, Netherlands

[73] Assignee: U.S. Philips Corporation, New York, N.Y.

[21] Appl. No.: 812,245

[22] Filed: Jul. 1, 1977

[30] Foreign Application Priority Data

Jul. 13, 1976 Netherlands .................... 7607723

[51] Int. Cl.² .............................................. C09K 11/46
[52] U.S. Cl. ............................... 252/301.4 H; 313/486
[58] Field of Search ................. 252/301.4 H; 313/486

[56] References Cited

U.S. PATENT DOCUMENTS

| 2,806,002 | 9/1957 | Smith .................... 252/301.4 H X |
| 2,855,325 | 10/1958 | Bentley .................. 252/301.4 H X |
| 3,506,584 | 4/1970 | Held et al. ............... 252/301.4 H |
| 3,667,921 | 6/1972 | Grodkiewicz et al. ... 252/301.4 H X |
| 3,702,828 | 11/1972 | Hoffman ................. 252/301.4 H |

OTHER PUBLICATIONS

Klasens et al., "Philips Research Reports," 8, pp. 441-451, 1953.
Sommerdijk et al., "J. Lumm.," 1975, 10(2), pp. 145-147.
"J. Lumm.," II, 1976, p. 363.
Bodrug et al., "Chem. Abstracts," vol. 78, 1973, 130168g.

*Primary Examiner*—Jack Cooper
*Attorney, Agent, or Firm*—Frank R. Trifari; Norman N. Spain

[57] ABSTRACT

Luminescent bivalent europium-activated fluoride according to the formula $$AB_{1-x-y}Mg_xEu_yF_3,$$

wherein A represents cesium and/or rubidium and B represents calcium and/or strontium and wherein
0.10 ≤ $x$ ≤ 0.90
0.001 ≤ $y$ ≤ 0.20
$x + y$ ≤ 0.95.

3 Claims, 4 Drawing Figures

LUMINESCENT FLUORIDE

The invention relates to a luminescent screen provided with a luminescent bivalent europium-activated fluoride of an alkali metal and an alkaline earth metal. Furthermore the invention relates to such a luminescent fluoride.

Fluorides which satisfy the general formula $Me^I\cdot Me^{II}F_3$, wheren $Me^I$ represents an alkali metal such as sodium, potassium, rubidium or cesium and $Me^{II}$ an alkaline earth metal such as magnesium, calcium or strontium, are known materials which have the cubic crystal structure of perovskite. An article in Philips Research Reports 8 (1953) page 441 discloses the activation of these fluorides by manganese. Materials are then obtained which, on excitation, luminesce with an emission colour varying, depending on the chosen host lattice from orange to green.

Activating the above-mentioned fluoride host lattices by bivalent europium is also known (see J. Luminescence, 10 (1975) page 145 and J. Luminescence, 11 (1976) page 363. It appears that the materials wherein magnesium is chosen for the element indicated by $Me^{II}$ have a line emission with a maximum in the spectrum at approximately 360 nm. However, at room temperature this luminescence is of low efficiency so that these materials are not eligible for practical applications. The fluorides wherein calcium or strontium is used for the element $Me^{II}$ have band emission in the blue or green portion of the spectrum, depending on the choice of the elements $Me^I$ and $Me^{II}$. With the exception of $CsCaF_3(Eu^{2+})$ these materials all have a low quantum efficiency so that they are not very suitable in practice. Bivalent europium activated $CsCaF_3$ luminesces comparatively efficiently with a maximum of the emission band at approximately 510 nm and with a quantum efficiency of approximately 30% (at 260 nm excitation) and approximately 60% (at 380 nm-excitation).

It is an object of the invention to provide new bivalent europium-activated fluorides which luminesce more efficiently than the above mentioned $CsCaF_3$ and which, owing to the efficient band emission in the blue or green portion of the spectrum can be used with much advantage in the luminescent screen of, for example, discharge lamps.

A luminescent screen according to the invention is provided with a luminescent bivalent europium-activated fluoride of an alkali metal and of an alkaline earth metal and is characterized in that the fluoride satisfies the formula

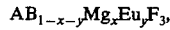

$AB_{1-x-y}Mg_xEu_yF_3$, wherein A represents cesium and/or rubidium and B represents calcium and/or strontium and wherein $0.10 \leq x \leq 0.90$
$0.001 \leq y \leq 0.20$
$x + y \leq 0.95$ As the general formula and conditions stated above show, a luminescent screen according to the invention is provided with a fluoride which always contains as alkaline earth metal a quantity of magnesium in combination with calcium and/or strontium. It was surprisingly found that these Mg-containing, mixed fluorides have much higher quantum efficiencies than both the pure alkali strontium and alkali calcium fluorides and the pure alkali magnesium fluorides. It was furthermore found that in all fluorides according to the invention a shift occurs in the location of the emission band relative to that of the pure fluorides, which was completely unexpected.

High quantum efficiencies in fluorides according to the invention are already found at comparatively small quantities of Mg. To obtain a sufficient effect of the Mg addition the concentration of this element should, however, not be smaller than 0.10. Also with very high concentrations of Mg, fluorides are obtained with high quantum efficiencies and with an emission which deviates from the line emission of the known pure alkali magnesium fluorides. In that case, however, the Mg-content, $x$ should be smaller or equal to 0.90. The europium concentration in the fluorides according to the invention can be chosen between the above-mentioned wide limits. For values of the Eu-concentration, $y$, smaller than 0.001, materials are obtained whose luminous flux is too low because then too small an absorption of the exciting radiation occurs. Values for $y$ exceeding 0.20 furnish materials which have too small a luminous flux owing to concentration quenching. The sum of Mg and Eu concentration in the materials according to the invention is chosen not in excess of 0.95 because otherwise the emission of the pure alkali magnesium fluorides may start dominating.

The luminescent fluorides according to the invention have in general, just like the pure fluorides, a crystal structure on the basis of perovskite. For the materials according to the invention it is assumed, however, that deviations from the ideal perovskite structure may occur.

It was found that the luminescent fluorides according to the invention can be propertly excited by ultravioler radiation, for example short wave ultra-violet radiation (at approximately 260 nm) and, in particular, by long-wave ultra-violet radiation (approximately 365 nm). As a consequence these fluorides can be used with much advantage in the luminescent screen of low-pressure mercury vapour discharge lamps and in the screen of high-pressure mercury vapour discharge lamps in particular. In connection with said last application it was surprisingly found that the fluorides according to the invention have a very favourable temperature dependency of the luminescence in contra-distinction with the known pure alkali-alkaline earth fluorides.

Preference is given to a luminescent screen which comprises a luminescent fluoride according to the above-mentioned general formula in which the conditions $0.50 \leq x \leq 0.80$ and $0.01 \leq y \leq 0.10$ are satisfied. The highest luminous fluxes are namely obtained with these fluorides.

Particularly high luminous fluxes are obtained with fluorides according to the invention in which cesium is chosen for A and calcium for B. Such materials are therefore preferred.

The luminescent fluorides according to the invention can be prepared by solid state reaction at a high temperature of a mixture of starting materials containing the composite elements. In general the fluorides of the elements A and B and europium trifluoride are used in this starting mixture. The reaction takes place by heating the starting mixture, for example for one or more hours, to a temperature of between 500° and 900° C in a weakly reducing atmosphere. Often preference should be given to performing this heating operation in several stages, the reaction product being cooled and homogenized in the intervals. Applying the fluorides to the support of a luminescent screen can be done in a generally known manner, for example starting from a suspension containing the fluoride.

Embodiments of the invention will now be further shown with reference to a drawing, an example of preparing the material and a number of measurements.

In the drawing

FIG. 1 shows the spectral energy distribution of the emitted radiation (on excitation by ultraviolet radiation having a wavelength of approximately 260 nm) of a luminescent fluoride according to the formula $CsCa_{0.25}Eu_{0.05}Mg_{0.70}F_3$. The wavelength 2 is plotted in nm on the horizontal axis. The radiation energy E is plotted in arbitrary units on the vertical axis. For reasons of comparison this Figure also shows the spectral energy distribution of the pure fluorides (not according to the invention): $CsMg_{0.95}Eu_{0.05}F_3$ (of which only the principal emission line is shown and $CsCa_{0.95}Eu_{0.05}F_3$. The maximum emission is set at 100 for each curve.

EXAMPLE

A mixture is made of
3.038 g CsF
0.392 g $CaF_2$
0.872 g $MgF_2$
0.209 g $EuF_3$ This mixture is heated in a platinum crucible in an oven for 2 hours at 600° C in a weakly reducing atmosphere consisting of nitrogen with 2% by volume of hydrogen. After cooling and homogenizing the reaction product is again heated for two hours in the same firing atmosphere, now however at 700° C. After cooling and pulverizing the product is ready for use. It consists of a luminescent fluoride according to the formula $CsCa_{0.25}Mg_{0.70}Eu_{0.05}F_3$. It appears that this material luminesces in a band having a maximum ($\lambda$ max) at 475 nm and half-value width ($\lambda \frac{1}{2}$) of 65 nm. The quantum efficiency on excitation with mainly 260 nm radiation ($q_{260}$) appears to be 45% and the quantum efficiency on excitation with mainly 365 nm-radiation ($q_{365}$) is 70%. This material posseses a very favourable temperature dependency of the luminescence. Namely, the ratio between the luminescent intensity at 300° C to that at 25° C ($I_{300}/I_{25}$) appears to be 90%.

In an analogous manner as indicated in the above example a great number of luminescent fluorides according to the invention were prepared. Measuring results of these materials ($\lambda$ max, $\lambda \frac{1}{2}$, $q_{260}$, $q_{365}$ and $I_{300}/I_{25}$) are shown in the tables which follow below. The formula of the relevant material is stated above each table, the magnesium content x being specified in the first column of each table. The materials a, b, c, d, e, f, g and h are pure alkaline earth alkali fluorides (not in accordance with the invention) and have only been included for comparison.

TABLE $CsCa_{0.95-x}Mg_xEu_{0.05}F_3$

| Example | x | $\lambda$ max (nm) | $\lambda \frac{1}{2}$ (nm) | $q_{260}(\%)$ | $q_{365}(\%)$ | $I_{300}/I_{25}(\%)$ |
|---|---|---|---|---|---|---|
| a[1] | 0 | 510 | 130 | 30 | 50 | <5 |

TABLE-continued $CsCa_{0.95-x}Mg_xEu_{0.05}F_3$

| Example | x | $\lambda$ max (nm) | $\lambda \frac{1}{2}$ (nm) | $q_{260}(\%)$ | $q_{365}(\%)$ | $I_{300}/I_{25}(\%)$ |
|---|---|---|---|---|---|---|
| 1 | 0.2 | 480 | 110 | 20 | 35 | — |
| 2 | 0.5 | 475 | 75 | 30 | 50 | 75 |
| 3[2] | 0.7 | 475 | 65 | 45 | 70 | 90 |
| 4 | 0.8 | 475 | 65 | 45 | 70 | 90 |
| 5 | 0.9 | 475 | 65 | 30 | 50 | — |
| b[3] | 0.95 | 360 | 1 | 1 | <1 | <5 |

Figure 1:
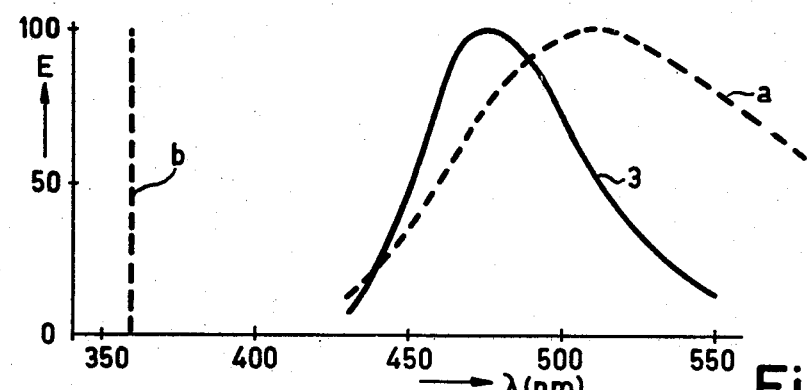

[1]Not according to the invention. See the dotted curve a in FIG. 1 for the spectral energy distribution of this material.
[2]See the curve 3 in FIG. 1 for the spectral energy distribution of this material.
[3]Not according to the invention. See the dotted curve b in FIG. 1 for the spectral energy distribution of this material.

TABLE 2

$RbCa_{0.95-x}Mg_xEu_{0.05}F_3$

| Example | x | $\lambda$ max (nm) | $\lambda \frac{1}{2}$ (nm) | $q_{260}(\%)$ | $q_{365}(\%)$ | $I_{300}/I_{25}(\%)$ |
|---|---|---|---|---|---|---|
| c[1] | 0 | 475 | 80 | <1 | 1 | <5 |
| 6 | 0.3 | 480 | 115 | 5 | 5 | — |
| 7 | 0.4 | 490 | 100 | 15 | 40 | 20 |
| 8[2] | 0.5 | 515 | 95 | 30 | 50 | 70 |
| 9 | 0.6 | 515 | 95 | 30 | 50 | 70 |
| 10 | 0.7 | 515 | 95 | 30 | 50 | 70 |
| 11 | 0.8 | 520 | 105 | 25 | 40 | — |
| d[3] | 0.95 | 360 | 1 | 3 | <1 | <5 |

Figure 2:
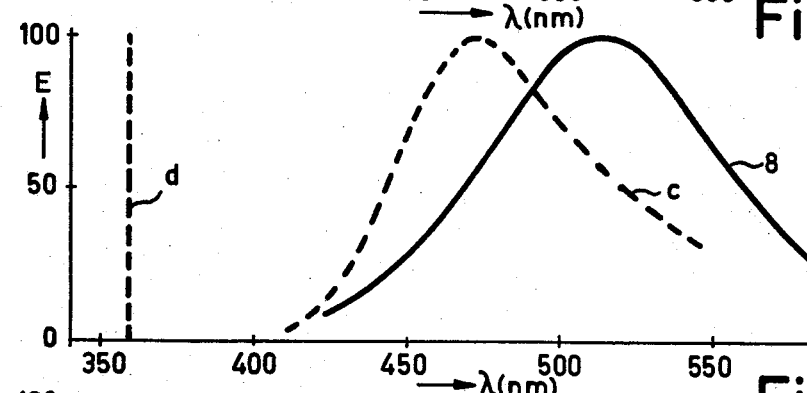
FIG. 2 shows the spectral energy distribution of the fluorides according to the formula $RbCa_{0.45}Mg_{0.50}Eu_{0.05}F_3$ in the same manner as FIG. 1.

[1]Not according to the invention. See dotted curve c in FIG. 2 for spectral energy distribution.
[2]See curve 8 in FIG. 2 for spectral energy distribution.
[3]Not according to the invention. See dotted curve d in FIG. 2 for spectral energy distribution.

TABLE 3

$CsSr_{0.95-x}Mg_xEu_{0.05}F_3$

| Example | x | $\lambda$ max (nm) | $\lambda \frac{1}{2}$ (nm) | $q_{260}(\%)$ | $q_{365}(\%)$ | $I_{300}/I_{25}(\%)$ |
|---|---|---|---|---|---|---|
| e[1] | 0 | 425 | 55 | 2 | 1 | <5 |
| 12 | 0.3 | 425 | 90 | 7 | 10 | — |
| 13 | 0.5 | 480 | 70 | 15 | 45 | 60 |
| 14[2] | 0.7 | 480 | 65 | 25 | 50 | 80 |
| f[3] | 0.95 | 360 | 1 | 1 | <1 | <5 |

Figure 3:
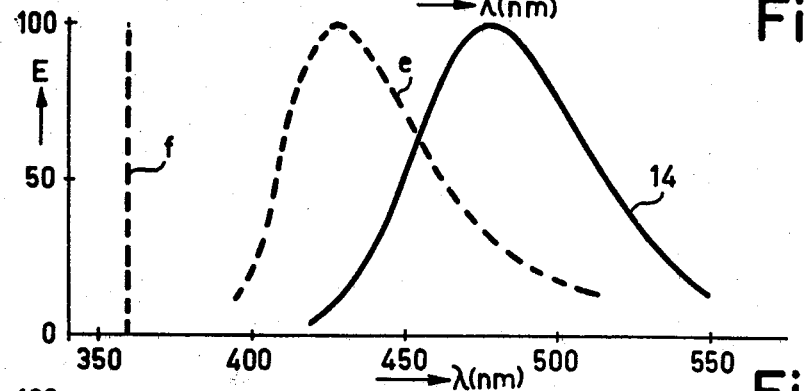
FIG. 3 shows the spectral energy distribution of $CsSr_{0.25}Mg_{0.70}Eu_{0.05}F_3$

[1]Not according to the invention. See dotted curve e in FIG. 3 for spectral energy distribution.
[2]See curve 14 in FIG. 3 for spectral energy distribution.
[3]Not according to the invention. See dotted curve f in FIG. 3 for spectral energy distribution.

TABLE 4

$RbSr_{0.95-x}Mg_xEu_{0.05}F_3$

| Example | x | $\lambda$ max (nm) | $\lambda \frac{1}{2}$ (nm) | $q_{260}(\%)$ | $q_{365}(\%)$ | $I_{300}/I_{25}(\%)$ |
|---|---|---|---|---|---|---|
| g[1] | 0 | 425 | 55 | <1 | <1 | <5 |
| 15 | 0.3 | 425 | 35 | 5 | 5 | — |
| 16[2] | 0.5 | 520 | 95 | 15 | 45 | 10 |
| 17 | 0.7 | 520 | 95 | 10 | 50 | 10 |
| h[3] | 0.95 | 360 | 1 | 3 | <1 | <5 |

Figure 4:
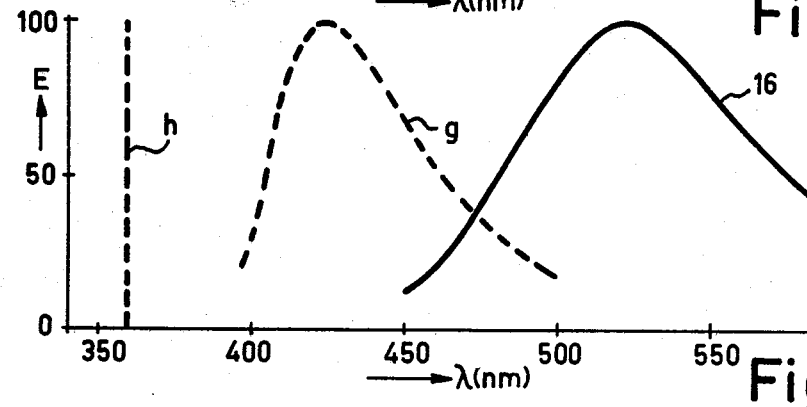
FIG. 4 shows the spectral energy distribution of $RbSr_{0.45}Mg_{0.50}Eu_{0.05}F_3$.

[1]Not according to the invention. See dotted curve g in FIG. 4 for spectral energy distribution.
[2]See curve 16 in FIG. 4 for spectral energy distribution.
[3]Not according to the invention. See dotted curve h in FIG. 4 for spectral energy distribution.

TABLE 5

$Cs_{1-p}Rb_pCa_{0.25}Mg_{0.7}Eu_{0.05}F_3$

| Example | p | $\lambda$ max (nm) | $\lambda \frac{1}{2}$ (nm) | $q_{260}(\%)$ | $q_{365}(\%)$ |
|---|---|---|---|---|---|
| 18 | 0.3 | 495 | 90 | 40 | 40 |
| 19 | 0.5 | 500 | 95 | 40 | 40 |
| 20 | 0.7 | 505 | 90 | 25 | 35 |

What is claimed is:

1. A luminescent bivalent europium-activated fluoride according to the formula $$AB_{1-x-y}Mg_xEu_yF_3,$$

wherein A represents cesium and/or rubidium and B represents calcium and/or strontium and wherein $0.10 \leq x \leq 0.90$
$0.001 \leq y \leq 0.20$
$x + y \leq 0.95;$ said luminescent fluoride having a higher quantum efficiency than the corresponding luminescent fluoride of the above formula in which either Mg or B is absent therefrom.

2. A luminescent fluoride as claimed in claim 1, characterized in that $0.50 \leq x \leq 0.80$
$0.01 \leq y \leq 0.10$ 3. A luminescent fluoride as claimed in claim 1, characterized in that A is cesium and B is calcium.

* * * * *